United States Patent
Miller et al.

(10) Patent No.: US 10,209,254 B2
(45) Date of Patent: Feb. 19, 2019

(54) CHIPS, DETECTION SYSTEMS, AND METHODS FOR MULTIPLEX PNEUMOCOCCUS SEROLOGY

(71) Applicants: UNIVERSITY OF ROCHESTER, Rochester, NY (US); THE UAB RESEARCH FOUNDATION, Birmingham, AL (US)

(72) Inventors: Benjamin L. Miller, Penfield, NY (US); Moon H. Nahm, Birmingham, AL (US)

(73) Assignees: University of Rochester, Rochester, NY (US); The UAB Research Foundation, Birmingham, AL (US)

( * ) Notice: Subject to any disclaimer, the term of this patent is extended or adjusted under 35 U.S.C. 154(b) by 0 days.

(21) Appl. No.: 15/028,370

(22) PCT Filed: Oct. 9, 2014

(86) PCT No.: PCT/US2014/059934
§ 371 (c)(1),
(2) Date: Apr. 8, 2016

(87) PCT Pub. No.: WO2015/054515
PCT Pub. Date: Apr. 16, 2015

(65) Prior Publication Data
US 2016/0258949 A1  Sep. 8, 2016

Related U.S. Application Data

(60) Provisional application No. 61/888,806, filed on Oct. 9, 2013.

(51) Int. Cl.
| | |
|---|---|
| *C40B 30/04* | (2006.01) |
| *G01N 33/569* | (2006.01) |
| *G01N 33/543* | (2006.01) |
| *G01N 21/21* | (2006.01) |
| *G01N 21/55* | (2014.01) |

(52) U.S. Cl.
CPC ..... *G01N 33/56944* (2013.01); *G01N 21/211* (2013.01); *G01N 21/55* (2013.01); *G01N 33/54373* (2013.01); *G01N 2201/0683* (2013.01); *G01N 2201/06113* (2013.01); *G01N 2333/3156* (2013.01)

(58) Field of Classification Search
None
See application file for complete search history.

(56) References Cited

U.S. PATENT DOCUMENTS

| 6,594,011 B1 | 7/2003 | Kempen |
|---|---|---|
| 2002/0192680 A1 | 12/2002 | Chan et al. |
| 2003/0112446 A1 | 6/2003 | Miller et al. |
| 2009/0275016 A1 | 11/2009 | Miller et al. |
| 2010/0047263 A1 | 2/2010 | Nagy et al. |
| 2010/0234281 A1 | 9/2010 | Weller et al. |
| 2011/0275532 A1 | 11/2011 | Mace et al. |

FOREIGN PATENT DOCUMENTS

| JP | 2003-525250 A | 8/2003 |
|---|---|---|
| WO | 2013/115962 A2 | 8/2013 |
| WO | 2015/106226 A2 | 7/2015 |

OTHER PUBLICATIONS

Chan et al., "Identification of Gram Negative Bacteria Using Nanoscale Silicon Microcavities," J. Am. Chem. Soc. 123:11797-11798 (2001).
Extended European Search Report for European Patent Application No. 14851985.3 (dated Apr. 4, 2017).
Horner et al., "A Proteomic Biosensor for Enteropathogenic E. coli," Biosensors and Bioelectronics 21:1659-1663 (2006).
Mace et al., "Label-Free, Arrayed Sensing of Immune Response to Influenza Antigens," Talanta 83:1000-1005 (2011).
Mace et al., "Theoretical and Experimental Analysis of Arrayed Imaging Reflectometry as a Sensitive Proteomics Technique," Anal. Chem. 78:5578-5583 (2006).
Invitation to Pay Additional Fees for PCT Patent Application No. PCT/US14/59934 (dated Dec. 15, 2014).
International Preliminary Report on Patentability for PCT Patent Application No. PCT/US14/59934 (dated Apr. 12, 2016).
Yu et al., "Rapid Multiplex Assay for Serotyping Pneumococci with Monoclonal and Polyclonal Antibodies," Journal of Clinical Microbiology 43(1):156-162 (2005).
Notice of Reasons for Rejection for corresponding Japanese Patent Application No. 2016-547974 (dated Jul. 5, 2018).
Examination report for corresponding European Patent Application No. 14851985.3 (dated Mar. 15, 2018).
Baader et al., "Polysaccharide Microarrays with a CMOS Based Signal Detection Unit," Biosens. Bioelectron. doi:10.1016/j.bios.2010.01.021 (2010).
Sabin Vaccine Institute, Proceedings of the Third Regional Pneumococcal Symposium, Istanbul, Turkey http://www.sabin.org/sites/sabin.org/files/3rd%20Pneumococcal%20Symposium%20web.pdf (2008).
PCT International Search Report and Written Opinion corresponding to PCT/US2014/059934, filed Oct. 9, 2014, (dated Feb. 18, 2015).

*Primary Examiner* — Jana A Hines
*Assistant Examiner* — Khatol S Shahnan Shah
(74) *Attorney, Agent, or Firm* — LeClairRyan PLLC

(57) ABSTRACT

According to aspects illustrated herein, there are provided a sensor chip suitable for serological detection of *Streptococcus pneumoniae*, a method for detecting serotypes of *Streptococcus pneumoniae* using the sensor chip, a detection system that includes the sensor chip, and a method for detecting serotypes of *Streptococcus pneumoniae* using the detection system described herein.

12 Claims, 8 Drawing Sheets

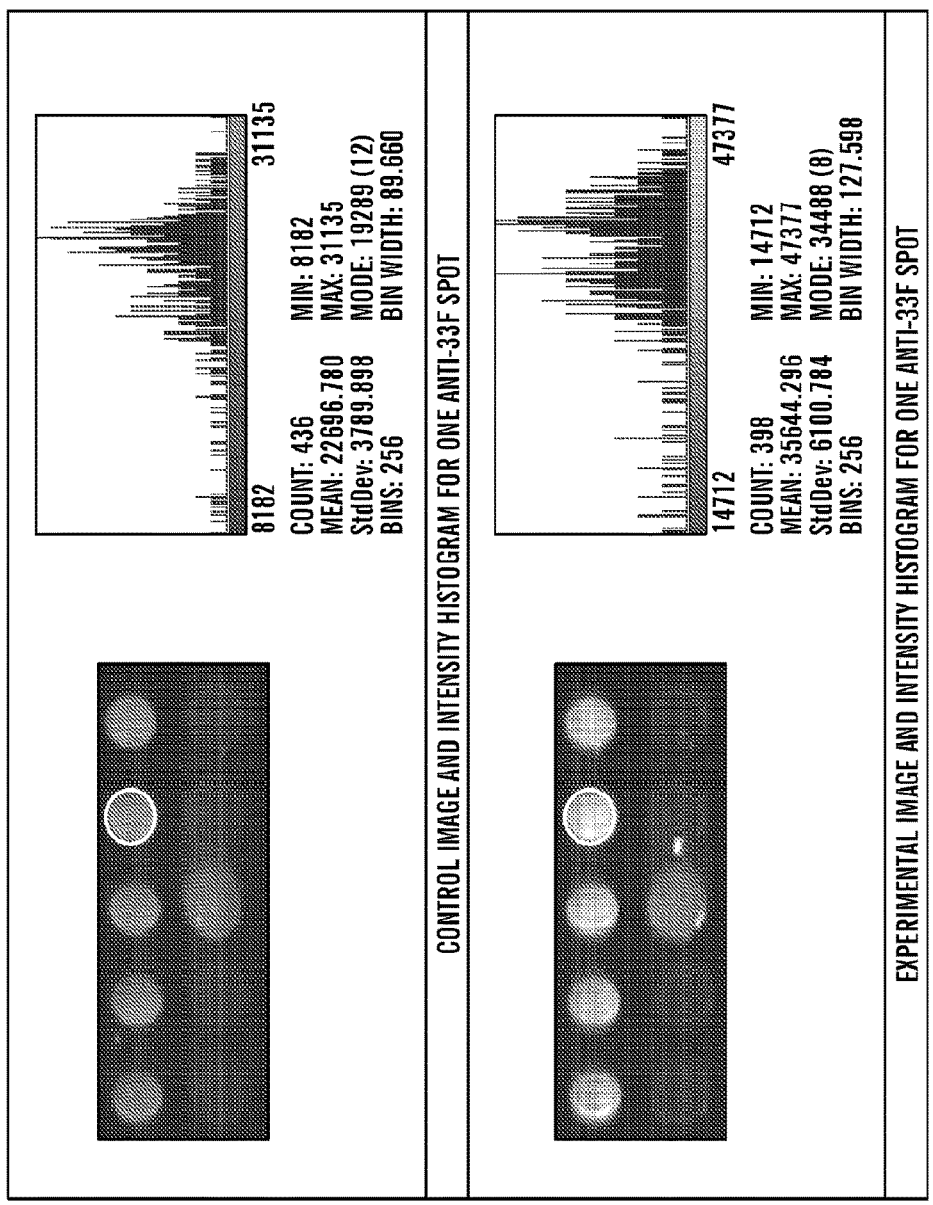

FIG. 8B

CHIPS, DETECTION SYSTEMS, AND METHODS FOR MULTIPLEX PNEUMOCOCCUS SEROLOGY

This application is a national stage application under 35 U.S.C. § 371 of PCT Application No. PCT/US2014/059934, filed Oct. 9, 2014, which claims the priority benefit of U.S. Provisional Patent Application Ser. No. 61/888,806, filed Oct. 9, 2013, which is hereby incorporated by reference in its entirety.

FIELD

According to aspects illustrated herein, there are provided sensor chips and detection systems for the serological detection of *Streptococcus pneumoniae* and methods of their use.

BACKGROUND

An ancillary development stemming from researchers' ability to produce and amplify recombinant proteins, and the genes from which they are encoded, is the high-throughput microarray. While initial applications of high-throughput screening focused on genomic arrays (Schena et al., "Quantitative Monitoring of Gene Expression Patterns With a Complementary DNA Microarray," *Science* 270:467-470 (1995), Lipshutz et al., "High density Synthetic Oligonucleotide Arrays," *Nat. Genet.* 21:20-24 (1999)), the protein microarray has found a variety of significant uses as well. For example, proteome profiling via protein microarrays has unveiled a myriad of novel interactions (MacBeath et al., "Printing Proteins as Microarrays for High-Throughput Function Determination," *Science* 289:1760-1763 (2000), Michaud et al., "Analyzing Antibody Specificity with Whole Proteome Microarrays," *Nat. Biotech.* 21:1509-1512 (2003) and Chan et al., "Protein Microarrays for Multiplexed Analysis of Signal Transduction Pathways," *Nat. Med.* 10:1390-1396 (2004)). Protein microarrays have been used to discover antigenic proteins and monitor human immunological responses to them (Davies et al., "Profiling the Humoral Immune Response to Infection by Using Proteome Microarrays: High-Throughput Vaccine and Diagnostic Antigen Discovery," *Proc. Natl. Acad. Sci. U.S.A.* 102:547-552 (2005); Li et al., "Protein Microarray for Profiling Antibody Responses to *Yersinia pestis* Live Vaccine," *Infect. Immun.* 73:3734-3739 (2005); and Qiu et al., "Antibody Responses to Individual Proteins of SARS Coronavirus and Their Neutralization Activities," *Microbes Infect.* 7:882-889 (2005)). This tactic has not been used previously for immobilization of multiple antibodies or antibody binding fragments for serological detection of *Streptococcus pneumoniae*. Moreover, in each of these reports, detection was achieved using labeled reagents.

Previous reports (Horner et al., "A Proteomic Biosensor for Enteropathogenic *E. coli*," *Biosen. Bioelect.* 21:1659-1663 (2006) and Mace et al., "Theoretical and Experimental Analysis of Arrayed Imaging Reflectometry as a Sensitive Proteomics Technique," *Anal. Chem.* 78:5578-5583 (2006)) describe arrayed imaging reflectometry detection of two interacting proteins, but have been unable to provide full serotype-level identification. Likewise, Chan et al., "Identification of Gram Negative Bacteria Using Nanoscale Silicon Microcavities," *J. Am. Chem. Soc.* 123:11797-11798 (2001), acknowledges that a liposaccharide sensor is not able to discriminate between different types of Gram-(−) bacteria. There has been some doubt as to whether, e.g., arrayed imaging reflectometry of capsular polysaccharides would be defeated by non-specific binding.

*Streptococcus pneumoniae* continues to be an exceptionally important human pathogen. Of the estimated 1.3 million global cases of childhood pneumonia in 2011 leading to death, 18.3% (237,900) were caused by *S. pneumoniae* (Fischer et al., "Global Burden of Childhood Pneumonia and Diarrhea," *Lancet* 381:1405-1416 (2013)). Pneumococcal pneumonia is also a significant problem in adults (Said et al., "Estimating the Burden of Pneumococcal Pneumonia among Adults: A Systematic Review and Meta-analysis of Diagnostic Techniques," *PLoS One* 8(4):e60273 (2013)). As more than 90 distinct serotypes of *S. pneumoniae* exist, the organism presents a substantial challenge to serology.

In addition to the traditional Quellung reaction method (Lund, "Laboratory Diagnosis of Pneumococcus Infections," *Bull. World Health Organ.* 23:5-13 (1960)), recent advances in *S. pneumoniae* detection have included the development of competition bead-based immunoassays (Yu et al., "A Rapid Pneumococcal Serotyping System Based on Monoclonal Antibodies and PCR," *J. Med. Microb.* 57:171-178 (2008)). While an important advance, such assays still require complex instrumentation and an equally complex workflow. Additionally, as with all sandwich immunoassays, increasing the number of serotypes covered by the assay is complicated by the need to re-qualify each component of the assay for cross-reactivity. PCR-based methods are widely used and popular, but these are indirect, complex, expensive, and there are recognized limitations to their strain coverage (Menezes et al., "Update of Pneumococcal 'PCR-Serotyping' for Detection of a Commonly Occurring Type 19F wzy Variant in Brazil," *J. Clin. Microbiol.* Doi:10.112/JCM.00743-13 (2013)).

Given the current state of the art and importance to human health, new serological methods for pneumococcus are clearly needed.

It would be desirable to provide an array of immobilized antibodies or antibody binding fragments that can be used to distinguish between different serotypes of *Streptococcus pneumoniae*.

SUMMARY

According to aspects illustrated herein, there is provided an arrayed imaging reflectometry ("AIR") sensor chip suitable for serological detection of *Streptococcus pneumoniae*. The sensor chip includes a multilayer substrate comprising a surface comprising bound thereon antibodies or antibody binding fragments that each bind specifically to one of two or more different serotypes of *Streptococcus pneumoniae*. The antibodies or antibody binding fragments are attached to the surface at different locations. The surface forms a coating that results in destructive interference of polarized light illuminating the surface at an appropriate incident angle and wavelength in the absence of *Streptococcus pneumoniae* binding. Exposure of the surface to a sample comprising *Streptococcus pneumoniae* to which the antibodies or antibody binding fragments bind produces a detectable change in reflectance at a location upon antibody or antibody binding fragment binding.

According to aspects illustrated herein, there is provided a method for detecting serotypes of *Streptococcus pneumoniae* using arrayed imaging reflectometry (AIR). This method involves providing a sensor chip as described herein. The sensor chip is contacted with a sample under conditions that permit specific binding to *Streptococcus pneumoniae* surface antigen by the antibodies or antibody binding fragments present on the chip surface. Light reflected off the surface of the chip is detected under conditions effective to identify specifically bound *Streptococcus pneumoniae* surface antigen, thereby detecting a serotype of *Streptococcus pneumoniae*.

According to aspects illustrated herein, there is provided a detection system. The detection system includes an arrayed imaging reflectometry (AIR) sensor chip suitable for serological detection of *Streptococcus pneumoniae* as described herein. Also included in the system is a light source that is positioned to illuminate the sensor chip. A detector is positioned to detect light reflected from the surface of the chip, and thereby determine specific binding to *Streptococcus pneumoniae* surface antigen by the antibodies or antibody binding fragments present on the chip surface. A destructive interference of polarized light illuminating the surface occurs in an absence of specific binding to *Streptococcus pneumoniae* surface antigen by the antibodies or antibody binding fragments to produce a change in reflectance detectable by the detector.

According to aspects illustrated herein, there is provided a method for serological detection of *Streptococcus pneumoniae*. This method involves providing a detection system as described herein. Light is directed at a surface of the sensor chip. The sensor chip is contacted with a sample under conditions that permit specific binding to *Streptococcus pneumoniae* surface antigen by the antibodies or antibody binding fragments present on the chip surface. Light reflected from the chip is detected under conditions effective to identify antibody-*Streptococcus pneumoniae* binding.

According to aspects illustrated herein, there is provided a sensor chip suitable for serological detection of *Streptococcus pneumoniae*. The sensor chip includes a substrate comprising a surface comprising bound thereon antibodies or antibody binding fragments that each bind specifically to one of two or more different serotypes of *Streptococcus pneumoniae*. The antibodies or antibody binding fragments are attached to the surface at different locations. The surface forms a coating that results in destructive interference of polarized light illuminating the surface at an appropriate incident angle and wavelength in the absence of *Streptococcus pneumoniae* binding. Exposure of the surface to a sample comprising *Streptococcus pneumoniae* to which the antibodies or antibody binding fragments bind produces a detectable change in reflectance at a location upon antibody or antibody binding fragment binding to *Streptococcus pneumoniae*.

One disclosed feature of the embodiments is a novel label-free antibody microarray that provides a simple, sensitive, and inexpensive solution to the problem of finding new serological methods for pneumococcus analysis. This disclosed feature allows expansion of the array to as many pneumococcal serotypes as desired without laborious requalification of secondary antibodies, and permits testing of samples for other organisms known to cause pneumonia, leading to a broadly useful diagnostic.

BRIEF DESCRIPTION OF THE DRAWINGS

FIG. 4A shows a thin film schematic and modeling variables. FIG. 4B is a graph showing simulated reflectance of a coated silicon chip in ambient air for I=633 nm laser source with the zero condition existing at a film thickness of d=1419 Å and q=70.6° incidence. FIG. 4C is a schematic illustration showing biodetection methodology, where molecular binding causes a strong reflectance increase from the zero condition.

FIG. 7 shows the detection of purified capsular polysaccharide. The upper panels provide a control image and intensity histogram for one anti-33F spot. The lower panels show the experimental image and intensity histogram for one anti-33F spot.

FIGS. 8A-B are images showing array performance and antibody cross-reactivity of one embodiment of AIR arrays as described herein. Preliminary results were expressed as a function of percentage of desired target thickness (intensity) for each serotype tested.

DETAILED DESCRIPTION

Figure 1:
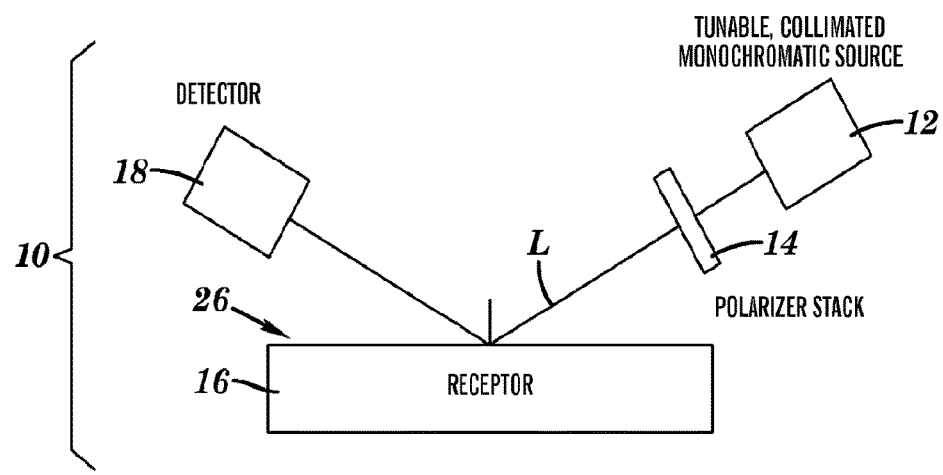
FIG. 1 is a schematic illustration of one embodiment of an AIR detection system.
Figure 2:
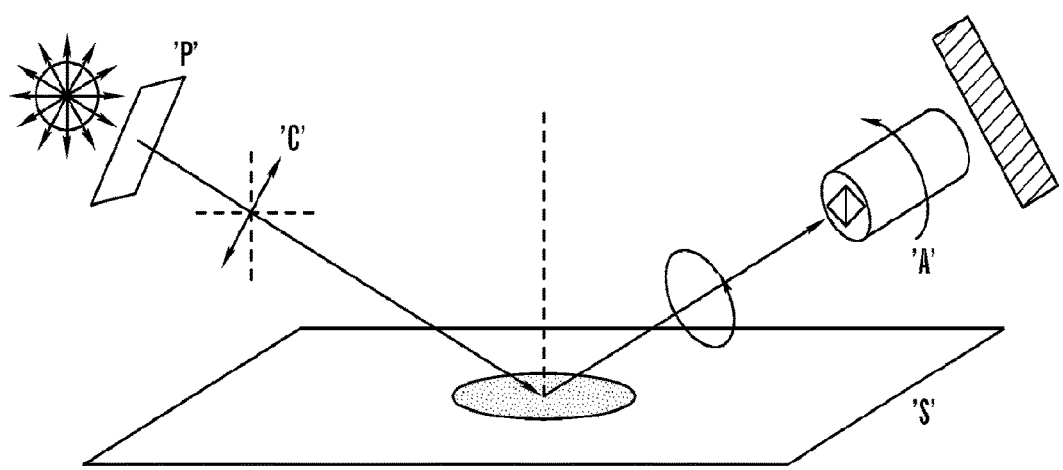
FIG. 2 is a schematic illustration of one embodiment of an ellipsometry detection system.

*Streptococcus pneumoniae* (the pneumococcus) is a human pathogen causing invasive diseases, such as pneumonia, bacteremia, and meningitis. *Streptococcus pneumoniae*, or pneumococcus, is a Gram-positive, alpha-hemolytic, bile-soluble aerotolerant, anaerobic member of the genus *Streptococcus*. A significant human pathogenic bacterium, *S. pneumoniae* was recognized as a major cause of pneumonia in the late 19th century, and is the subject of many humoral immunity studies.

*S. pneumoniae* can be differentiated from *Streptococcus viridans*, some of which are also alpha-hemolytic, using an optochin test, as *S. pneumoniae* is optochin-sensitive. *S. pneumoniae* can also be distinguished based on its sensitivity to lysis by bile. The encapsulated, Gram-positive coccoid bacteria have a distinctive morphology on Gram stain, the so-called, "lancet-shaped" diplococci. They have a polysaccharide capsule that acts as a virulence factor for the organism; more than 90 different serotypes are known, and these types differ in virulence, prevalence, and extent of drug resistance. Known serotypes of *S. pneumoniae* include serotypes 1, 2, 3, 4, 5, 6A, 6B, 7F, 7A, 7B, 7C, 8, 9A, 9L, 9N, 9V, 10F, 10A, a0B, 10C, 11F, 11A, 11B, 11C, 11D, 12F, 12A, 12B, 13, 14, 15F, 15A, 15B, 15C, 16F, 16A, 17F, 17A, 18F, 18A, 18B, 18C, 19F, 19A, 19B, 19C, 20, 21, 22F, 22A, 23F, 23A, 23B, 24F, 24A, 24B, 25F, 25A, 27, 28F, 28A, 29, 31, 32F, 32A, 33F, 33A, 33B, 33C, 33D, 34, 35F, 35A, 35B, 35C, 36, 37, 38, 39, 40, 41F, 41A, 42, 43, 44, 45, 46, 47F, 47A, and 48 (Bentley et al., "Genetic Analysis of the Capsular Biosynthetic Locus from All 90 Pneumococcal Serotypes," *PLoS Genet.* 2(3):e31 (2006), the disclosure of which is incorporated herein by reference in its entirety).

The genome of *S. pneumoniae* is a closed, circular DNA structure that contains between 2.0 and 2.1 million basepairs, depending on the strain. It has a core set of 1553 genes, plus 154 genes in its virulome, which contribute to virulence, and 176 genes that maintain a noninvasive phenotype. Genetic information can vary up to 10% between strains.

*S. pneumoniae* is part of the normal upper respiratory tract flora, but, as with many natural flora, it can become pathogenic under the right conditions (e.g., if the immune system of the host is suppressed). Invasins, such as pneumolysin, an antiphagocytic capsule, various adhesins, and immunogenic cell wall components are all major virulence factors.

Despite the availability of antibiotics, pneumococcal infections remain common and can still be fatal, especially in high-risk groups, such as young children and elderly people. Particularly in developing countries, many children under the age of five years die each year from pneumococcal pneumonia. *S. pneumoniae* is also the leading cause of otitis media and sinusitis. These infections are less serious, but nevertheless incur substantial medical costs, especially when leading to complications, such as permanent deafness. The normal ecological niche of the pneumococcus is the nasopharynx of man. The entire human population is colonized by the pneumococcus at one time or another, and at a given time, up to 60% of individuals may be carriers. Nasopharyngeal carriage of pneumococci by man is often accompanied by the development of protection against infection by the same serotype. Most infections do not occur after prolonged carriage but follow exposure to recently acquired strains. Many bacteria contain surface polysaccharides that act as a protective layer against the environment. Surface polysaccharides of pathogenic bacteria usually make the bacteria resistant to the defense mechanisms of the host, for example, the lytic action of serum or phagocytosis. In this respect, the serotype-specific capsular polysaccharide ("CP") of *Streptococcus pneumoniae*, is an important virulence factor. Unencapsulated strains are avirulent, and antibodies directed against the CP are protective. Protection is serotype specific; each serotype has its own, specific CP structure. Ninety different capsular serotypes have been identified. Currently, CPs of 23 serotypes are included in a vaccine.

Vaccines directed against *Streptococcus* infections typically aim to utilize an immune response directed against the polysaccharide capsule of the various *Streptococcus* serotypes, especially since the capsule is considered a primary virulence factor for these bacteria. During infection, the capsule provides resistance against phagocytosis and, thus, protects the bacteria from the immune system of the host, and from elimination by macrophages and neutrophils.

The capsule particularly confers the bacterium resistance to complement-mediated opsonophagocytosis. In addition, some bacteria express capsular polysaccharides (CPs) that mimic host molecules, thereby avoiding the immune system of the host. Also, even when the bacteria have been phagocytosed, intracellular killing is hampered by the presence of a capsule.

It is generally thought that the bacterium will be recognized by the immune system through the anticapsular-antibodies or serum-factors bound to its capsule, and will, through opsonization, be phagocytosed and killed only when the host has antibodies or other serum factors directed against capsule antigens.

However, these antibodies are serotype-specific, and will often only confer protection against only one of the many serotypes known within a group of Streptococci. For example, current commercially available *S. suis* vaccines, which are generally based on whole-cell-bacterial preparations, or on capsule-enriched fractions of *S. suis*, confer only limited protection against heterologous strains. Also, the current pneumococcal vaccine, which was licensed in the United States in 1983, includes purified CPs of 23 pneumococcal serotypes whereas at least 90 CP types exist. The composition of this pneumococcal vaccine was based on the frequency of the occurrence of disease isolates in the U.S. and cross-reactivity between various serotypes. Although this vaccine protects healthy adults against infections caused by serotypes included in the vaccine, it fails to raise a protective immune response in infants younger than 18 months and it is less effective in elderly people. In addition, the vaccine confers only limited protection in patients with immunodeficiencies and hematology malignancies.

Thus, improvements in serotype identification are needed to protect against *Streptococcus* infections. Much attention is directed toward producing CP vaccines by producing the relevant polysaccharides. As disclosed herein, a label-free antibody microarray that provides a simple, sensitive, and inexpensive solution to the problem of finding new serological methods for pneumococcus analysis will greatly assist this effort.

According to aspects illustrated herein, there is provided a sensor chip suitable for serological detection of *Streptococcus pneumoniae*. One disclosed feature of the embodiments is an arrayed imaging reflectometry (AIR) sensor chip suitable for serological detection of *Streptococcus pneumoniae*. The sensor chip includes a multilayer substrate comprising a surface comprising bound thereon antibodies or antibody binding fragments that each bind specifically to one of two or more different serotypes of *Streptococcus pneumoniae*. The antibodies or antibody binding fragments are attached to the surface at different locations. The surface forms a coating that results in destructive interference of polarized light illuminating the surface at an appropriate incident angle and wavelength in the absence of *Streptococcus pneumoniae* binding. Exposure of the surface to a sample comprising *Streptococcus pneumoniae* to which the antibodies or antibody binding fragments bind produces a detectable change in reflectance at a location upon antibody or antibody binding fragment binding.

In addition to being suitable for use in an Arrayed Imaging Reflectometry (AIR) detection system, the sensor chip may also be suitable for use in a surface plasmon resonance ("SPR") detection system, a Brewster Angle Straddle Interferometry ("BASI") detection system, and ellipsometry detection systems.

The overall design and construction of the sensor chip can be varied according to the particular detection system in which it is to be used. These include, for example and without limitation, sensors designed for use with AIR detection systems, SPR detection systems, BASI detection systems, and ellipsometry detection systems, as well as any other label-free or fluorescence labeled array technique.

An AIR detection system is described in U.S. Pat. No. 7,292,349 to Miller et al., the disclosure of which is incorporated herein by reference in its entirety. This setup is illustrated in FIG. 1. The system 10 includes a light source 12, a polarizer 14, a receptor 16 (i.e., the functionalized sensor chip as described herein), and a detector 18. The light source 12 generates and transmits a light (L) at set wavelengths towards a surface of the receptor. One or more lenses and filters can be employed to optimize the system. AIR exploits interference between reflections from the medium/coating and coating/substrate interfaces on the receptor, exhibiting changes in reflectivity upon binding of biomolecules to the coating. In practice, using a silicon wafer having an oxide coating, judicious choice of incident angle and wavelength can be used with s-polarized light to obtain near complete destructive interference (i.e., reflectivity that is, e.g., less than about $10^{-5}$ or even $10^{-6}$ under some circumstances) in the absence of a target, in this case different serotypes of *Streptococcus pneumoniae*. The condition of near complete (or near perfect) destructive interference is removed upon target binding. Thus, highly sensitive detection of even small quantities of different serotypes of *Streptococcus pneumoniae* is possible.

While AIR using s-polarized light has proven to be a highly sensitive, simple analytical method for the quantitative detection of a variety of biomolecular analytes, the system described in the above-referenced U.S. Pat. No. 7,292,349 to Miller et al. is much more easily carried out in a dry state, that is, with an air/oxide interface rather than with an aqueous/oxide interface. An improved system for performing AIR in an aqueous environment is described in U.S. Pat. No. 8,502,982 to Mace et al., the disclosure of which is incorporated herein by reference in its entirety. Basically, the flow cell as described therein allows for coupling of the s-polarized light into the aqueous environment for detection of target binding.

In both the wet and dry AIR systems, the sensor chip has the same fundamental construction, with a substrate, one or more coating layers on the substrate, and then the probe molecules—in this case antibodies or antibody binding fragments that each bind specifically to one of two or more different serotypes of *Streptococcus pneumoniae*—bound to the coating surface at discrete locations. As described in the above-referenced U.S. Pat. No. 7,292,349 to Miller et al. and U.S. Pat. No. 8,502,982 to Mace et al., the disclosures of which are incorporated herein by reference in their entirety, a number of different materials can be selected for the substrate and coating(s). Any suitable combination of substrates and coatings is contemplated for the sensor chip to be used in an AIR detection system. One example is a silicon substrate and a silicon dioxide coating.

According to one embodiment, there is provided a detection system that includes an arrayed imaging reflectometry (AIR) sensor chip suitable for serological detection of *Streptococcus pneumoniae* as described herein. Also included in the system is a light source that is positioned to illuminate the sensor chip. A detector is positioned to detect light reflected from the surface of the chip, and thereby determine specific binding to *Streptococcus pneumoniae* surface antigen by the antibodies or antibody binding fragments present on the chip surface. A destructive interference of polarized light illuminating the surface occurs in an absence of specific binding to *Streptococcus pneumoniae* surface antigen by the antibodies or antibody binding fragments to produce a change in reflectance detectable by the detector.

The BASI detection system is described in U.S. Pat. No. 7,551,294 to Rothberg, the disclosure of which is incorporated herein by reference in its entirety. The BASI system, like the AIR system, exploits interference between reflections from the medium/coating and coating/substrate interfaces, and exhibits changes in reflectivity upon binding of biomolecules to the coating. The basic design of the system is similar to that illustrated in FIG. 1 (for AIR), but the structure of the sensor chip differs. The BASI system is functional with any substrate/coating combinations where the coating is very thin (e.g., a native oxide film on silicon) and when the incidence angle on one of two interfaces (substrate/coating or coating/medium) is greater than its Brewster angle and the incidence angle on the other of the two interfaces is less than its Brewster angle. Unlike AIR systems being commercially developed for use with incident s-polarized light, the BASI system relies on the detection of p-polarized light. As a result of using Brewster angle straddle and p-polarized light, where the coating thickness is $\ll\lambda$, a phase flip of the reflected polarization allows nearly complete destructive interference (where reflectivity is e.g., less than about $10^{-4}$ or even $10^{-5}$ in the absence of target binding). As with the AIR detection system, sensitive detection of even small quantities of different serotypes of *Streptococcus pneumoniae* is possible.

Ellipsometric detection systems measure the polarization component of reflected light as a measure of changes in coating thickness on the surface of the sensor chip. Ellipsometry sensitively measures the change of the state of polarization when electromagnetic radiation is reflected or transmitted by a sample. A classical embodiment of such an ellipsometric detection system, illustrated in FIG. 2, includes a light source that emits a collimated light beam passing a variable polarization controller given by the combination of a linear polarizer (P) and a compensator in the form of a quarter-wave plate (C). The polarized light beam is incident on the sensor surface (S) under a known oblique angle, reflected from the sample surface and analyzed by a second linear polarizer coupled to a suitable photodetector (A, collectively). In this ellipsometer setup, the measurement may be done by changing the azimuths of the components P and A, while the optical axis of C is kept at a constant azimuth, e.g., at 45° with respect to the plane of incidence, until the photodetector receives a minimum of intensity. The azimuthal angles of the components P, C, and A for this "nulling" condition may be used to calculate the ellipsometric angles Delta and Psi, which are specific for the optical parameters of the sample at a given angle of incidence and wavelength of light. Using a suitable optical model and numerical regression, the quantities Delta and Psi may be recalculated in terms of the thickness of the optical layer, or changes thereof during a growth process. The application of ellipsometry for monitoring of binding reactions of biological molecules dates back to 1942 (Rothen et al., "Serological Reactions of Protein Films and Denatured Proteins," *J. Exp. Med* 76:437 (1942), the disclosure of which is incorporated herein by reference in its entirety), where the amount of adsorbed biological material at a surface during a binding reaction may be recalculated from the quantities Delta and Psi.

Imaging ellipsometry, as described for example in U.S. Pat. No. 5,076,696 to Cohn et al., the disclosure of which is incorporated herein by reference in its entirety, uses spatially resolving detector and imaging optics to allow for a massively parallel measurement of ellipsometric data, e.g., in the form of Delta and/or Psi maps. Such maps may in turn be converted into surface maps of layer thickness, optical index of refraction, chemical composition, or the amount of adsorbed material for each spot on an array. Imaging ellipsometry with its intrinsic parallel detection scheme may be used advantageously as a detection technique for these so-called biochips, microarrays, or microplates (Eing et al., *Imaging Ellipsometry in Biotechnology*, ISBN 3-9807279-6-3 (2002), the disclosure of which is incorporated herein by reference in its entirety).

Imaging ellipsometry has been demonstrated with light employed for the measurement impinging on the surface to be measured coming from the ambient medium. Other measurement setups are based on total internal reflection as described for example in U.S. Pat. No. 6,594,011 to Kempen, the disclosure of which is incorporated herein by reference in its entirety. Here, the light from a light source is directed through an internal reflection element to reflect off the specimen to be detected.

Figure 3A:
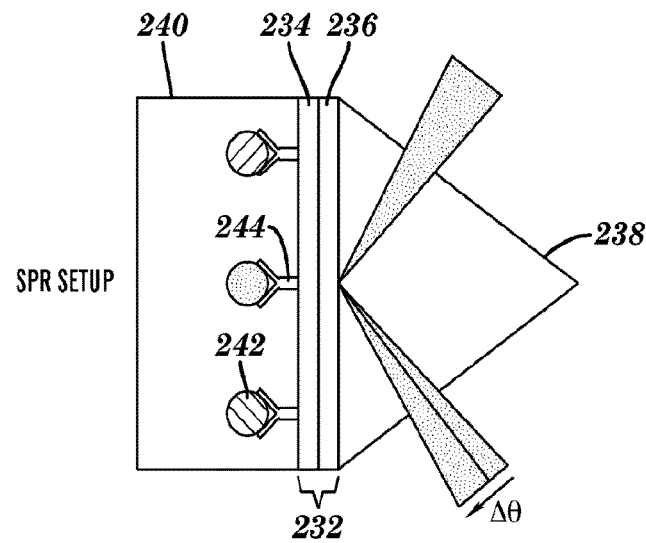
FIG. 3A is a schematic illustration of one embodiment of an SPR detection system.
Figure 3B:
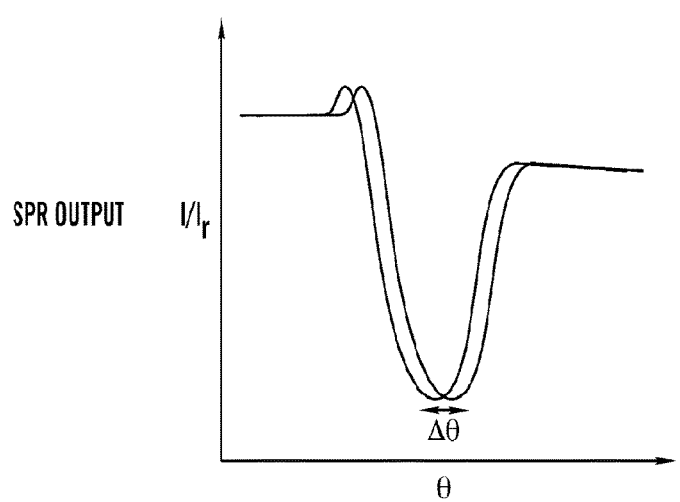
FIG. 3B illustrates the output of SPR.

Enhancement of the detection signal can be achieved using SPR ellipsometry, illustrated in FIG. 3A. The substrate 232 employed during SPR ellipsometry uses a thin metal layer 234 to allow the excitation and propagation of surface plasmons. While one side of the metal layer 234 is in contact with a transparent support structure 236, usually attached to a prism 238 allowing light to couple-in under an oblique angle, the other side of the layer is exposed to the ambient medium 240. Changes in the optical index of refraction in the ambient by the formation of an adsorbent layer (e.g., in this specific example surface-bound antibodies 244 binding to capsular polysaccharides 242 of three different serotypes) are monitored as a shift in the angle of incidence (Δθ) that generates surface plasmon resonance, causing a change of reflected light intensity (see FIG. 3B). For SPR based sensors, it is known that an intermediate dielectric layer between the metal film and the probed surface may act as a means to further increase the sensitivity.

Regardless of the sensor chip substrate or the detection system in which the substrate is intended to be used, the sensor chip includes antibodies or antibody binding fragments bound to the surface of the sensor chip.

A trait inherent to all biosensors, regardless of labeling status or means of signal transduction, is probe immobilization. The role of the terminal hydroxyl of a silicon dioxide surface is highly flexible as it may act as a nucleophile (Bikiaris et al., "Compatibilisation Effect of PP-g-MA Copolymer on iPP/SiO$_2$ Nanocomposites Prepared by Melt Mixing," *Eur. Polym. J.* 41:1965-1978 (2005); Tripp et al., "Chemical Attachment of Chlorosilanes to Silica: A Two-step Amine-promoted Reaction," *J. Phys. Chem.* 97:5693-5698 (1993), the disclosures of which are incorporated herein by reference in their entirety) or support adsorption. For this reason, silicon dioxide is readily derivitized through a variety of chemical methods. These chemical reactions result in the effective transformation of the hydroxyl group to any of a number of chemical functionalities including, but certainly not limited to, amines (Huang et al., "Directed Assembly of One-dimensional Nanostructures Into Functional Networks," *Science* 291:630-633 (2001), the disclosure of which is incorporated herein by reference in its entirety) or halides (Hergenrother et al., "Small-molecule Microarrays: Covalent Attachment and Screening of Alcohol-containing Small Molecules on Glass Slides," *J. Am. Chem. Soc.* 122:7849-7850 (2001), the disclosure of which is incorporated herein by reference in its entirety). From each initial reaction, a secondary chemical can be added to further alter the surface reactivity or probes may be directly coupled. Moreover, a multitude of functionalized silanes, molecules that couple to and self-assemble on silicon dioxide (Onclin et al., "Engineering Silicon Oxide Surfaces Using Self-assembled Monolayers," *Angew Chemie Int. Ed.* 44:2-24 (2005), the disclosure of which is incorporated herein by reference in its entirety), are commercially available, and may confer a diverse chemical landscape to the surface of the substrate (amines, epoxides, alkenes, etc.). A number of these approaches are generally described in U.S. Pat. No. 7,226,733 to Chan et al. and U.S. Pat. No. 7,292,349 to Miller et al., the disclosures of which are incorporated herein by reference in their entirety.

PCT Publication No. WO 2010/039808 to Mace et al., the disclosure of which is incorporated herein by reference in its entirety, teaches the use of a non-nucleophilic additive in a formulation containing a probe molecule to be bound to an array surface. The non-nucleophilic additive is used in an amount effective to avoid or reduce the severity of surface morphological anomalies caused by non-homogeneous distribution of the reactant across a spot on the array where the reactant is bound. These surface morphological anomalies include bright center spots and "coffee stain" rings (or halos) that can interfere with accurate detection of target molecule binding at a particular spot. In other words, the use of effective amounts of the non-nucleophilic additive promotes substantially homogeneous distribution of the reactant across each of the spots on the array where the probe is located. By homogeneous distribution, it is intended that the variance of reactant concentration across the surface of a spot is minimized (relative to spots prepared in the absence of the non-nucleophilic additives). Stated another way, there is e.g., less than about 10 percent pixel variation across the array spot, or less than about 5 percent variation, or less than about 3 percent variation, 2 percent variation, or even less than about 1 percent variation.

Any effective amount of non-nucleophilic additive can be used. Typically, such an effective amount is between about 0.001 to about 3 percent v/v, or between about 0.01 to about 1 percent v/v.

One embodiment of the non-nucleophilic additive includes compounds having a structure of formula (I) as follows:

$$R^1-O-[(CH_2)_mO]_n-R^2 \quad (I)$$

where, n is an integer from 0 to about 250; m is an integer from 1 to 3, or 1 or 2; and $R^1$ and $R^2$ are independently selected from the group of a C1 to C3 alkyl, or $R^1$ and $R^2$ together form a C1 to C3 alkyl, in which case the compound of formula (I) has a cyclic structure. $R^1$ and $R^2$ are, according to one embodiment, methyl or ethyl, or together form an ethyl group. These additives may have a molecular weight that is about 5000 Da or less, or about 4000 Da or less, or about 3000 Da or less, or about 2000 Da or less, or even about 1000 Da or less. Exemplary non-nucleophilic additives of formula (I) include, without limitation, crown ethers (18-Crown-6, 15-Crown-5, 12 Crown-4, etc.), bis(2-methoxyethyl) ether, dialkyl ethers, and polyethylene glycol.

According to another embodiment, the non-nucleophilic additive is dimethylsulfoxide (DMSO).

The benefit of employing the non-nucleophilic additives, which do not participate in the chemical coupling of a reactant (or probe precursor) to the functionalized chip substrate, is that the additives promote better dispersion of the probe molecules across their respective discrete locations on the array. This improved dispersion consequently minimizes or entirely avoids the presence of surface morphological anomalies that can decrease the sensitivity of the detection system. As a result, improved sensitivity for the detection of target molecules can be achieved.

In terms of distinguishing serotypes, antibodies to *S. pneumoniae* are currently available, and antibodies to many serotypes have been described in the literature (see, e.g., Yu et al., "Development of an Automated and Multiplexed Serotyping Assay for *Streptococcus pneumoniae*," *Clinical and Vaccine Immunology* 18:1900-1907 (2011); Yu et al., "A Rapid Pneumococcal Serotyping System Based on Monoclonal Antibodies and PCR," *J. Med. Microbiol.* 57:171-178 (2008); and Yu et al., "Rapid Multiplex Assay for Serotyping Pneumococci with Monoclonal and Polyclonal Antibodies," *J. Clin. Microbiol.* 43:156 (2005); the disclosures of which are incorporated herein by reference in their entirety).

According to one embodiment, the antibodies or antibody binding fragments bind specifically to pneumococcal polysaccharides. In one embodiment, specific binding to *Streptoccocus pneumoniae* is to a surface antigen of the bacterium. Thus, specific binding need not be to the whole bacterium. By "surface antigen," it is meant that the antigen is normally surface exposed on the bacterium, but when present in a sample it may be isolated or recovered from the bacterium.

In one embodiment, the pneumococcal polysaccharides are full length polysaccharides and in other embodiment the pneumococcal polysaccharides are polysaccharide fragments. When the antibodies or antibody binding fragments bind to pneumococcal polysaccharide fragments, each fragment comprises an epitope to which at least one of the antibodies or antibody binding fragments bind.

Antibodies suitable for the sensor chip may be purchased or prepared. Means for preparing and characterizing antibodies are well known in the art (see, e.g., *Antibodies: A Laboratory Manual*, Cold Spring Harbor Laboratory, 1988, and U.S. Pat. No. 4,196,265, the disclosures of which are incorporated herein by reference in their entirety).

The term "antibody" as used herein is any specific binding substance having a binding domain with the required specificity. Thus, this term is meant to include intact immunoglobulins derived from natural sources or from recombinant sources, as well as immunoreactive portions (i.e., binding portions) of intact immunoglobulins. Antibodies may exist in a variety of forms including, for example, polyclonal antibodies, monoclonal antibodies, intracellular antibodies ("intrabodies"), antibody fragments (e.g., Fv, Fab and F(ab) 2), as well as single chain antibodies (scFv), chimeric antibodies, and humanized antibodies (Ed Harlow and David Lane, USING ANTIBODIES: A LABORATORY MANUAL (Cold Spring Harbor Laboratory Press, 1999); Houston et al., "Protein Engineering of Antibody Binding Sites: Recovery of Specific Activity in an Anti-Digoxin Single-Chain Fv Analogue Produced in *Escherichia coli*," *Proc. Natl. Acad. Sci. USA* 85:5879-5883 (1988); Bird et al, "Single-Chain Antigen-Binding Proteins," *Science* 242:423-426 (1988), the disclosures of which are incorporated herein by reference in their entirety).

In addition to whole antibodies, binding portions of such antibodies are contemplated. Such binding portions include the monovalent Fab fragments, Fv fragments (e.g., single-chain antibody, scFv), and single variable $V_H$ and $V_L$ domains, and the bivalent $F(ab')_2$ fragments, Bis-scFv, diabodies, triabodies, minibodies, etc. These antibody fragments can be made by conventional procedures, such as proteolytic fragmentation procedures, as described in James Goding, MONOCLONAL ANTIBODIES: PRINCIPLES AND PRACTICE 98-118 (Academic Press, 1983) and Ed Harlow and David Lane, ANTIBODIES: A LABORATORY MANUAL (Cold Spring Harbor Laboratory, 1988), the disclosures of which are incorporated herein by reference in their entirety, or other methods known in the art.

As used herein, the phrase "bind(s) specifically to" means that the antibody or binding fragment thereof binds to the stated target (e.g., a pneumococcal polysaccharide of a one serotype of *Streptoccocus pneumoniae*) with more affinity than it binds to other targets. According to one embodiment, an antibody or binding fragment thereof that binds specifically to one of two more different serotypes of *Streptoccocus pneumoniae* binds to one and only one serotype of *Streptoccocus pneumoniae*. According to another embodiment, an antibody or binding fragment thereof that binds specifically to one of two more different serotypes of *Streptoccocus pneumoniae* binds to one serotype with greater affinity than it binds to any other serotypes of *Streptoccocus pneumoniae*.

The methods for generating monoclonal antibodies (MAbs) generally begin along the same lines as those for preparing polyclonal antibodies. The first step for both these methods is immunization of an appropriate host or identification of subjects who are immune due to prior natural infection. As is well known in the art, a given composition for immunization may vary in its immunogenicity. It is often necessary therefore to boost the host immune system, as may be achieved by coupling a peptide or polypeptide immunogen to a carrier. Exemplary carriers are keyhole limpet hemocyanin (KLH) and bovine serum albumin (BSA). Other albumins such as ovalbumin, mouse serum albumin, or rabbit serum albumin can also be used as carriers. Means for conjugating a polysaccharide to a carrier protein are well known in the art and include glutaraldehyde, m-maleimidobencoyl-N-hydroxysuccinimide ester, carbodiimide, and bis-biazotized benzidine. As also is well known in the art, the immunogenicity of a particular immunogen composition can be enhanced by the use of non-specific stimulators of the immune response, known as adjuvants. Exemplary adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous, and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

In the case of human monoclonal antibodies, one may instead simply look for an individual already known to have generated an immune response, in this case, to have been exposed to *S. pneumoniae* or immunized with Pneumovax®23.

Following immunization or obtaining of cells from previously infected subjects as described above, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures are e.g., non-antibody-producing, have high fusion efficiency, and enzyme deficiencies that render them incapable of growing in certain selective media which support the growth of only the desired fused cells (hybridomas).

Any one of a number of myeloma cells may be used, as are known to those of skill in the art. For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7, and S194/5XX0 Bul; for rats, one may use R210.RCY3, Y3-Ag 1.2.3, IR983F, and 4B210; and U-266, GM1500-GRG2, LICR-LON-HMy2, and UC729-6 are all useful in connection with human cell fusions. One particular murine myeloma cell is the NS-1 myeloma cell line (also termed P3-NS-1-Ag-4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line. More recently, additional fusion partner lines for use with human B cells have been described, including KR12 (ATCC CRL-8658), K6H6/B5 (ATCC CRL-1823), SHM-D33 (ATCC CRL-1668), and HMMA2.5.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes.

Fusion procedures usually produce viable hybrids at low frequencies, about $1\times10^{-6}$ to $1\times10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus ("EBV") transformed human B cell line, in order to eliminate EBV transformed lines that have not fused to the myeloma.

According to one embodiment, the selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase ("HPRT"), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain is also used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple, and rapid, such as radioimmunoassays, enzyme immunoassays, cytotoxicity assays, plaque assays dot immunobinding assays, and the like.

The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cell lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation, and various chromatographic methods such as FPLC or affinity chromatography.

Fragments of the monoclonal antibodies can be obtained from the purified monoclonal antibodies by methods which include digestion with enzymes, such as pepsin or papain, and/or by cleavage of disulfide bonds by chemical reduction. Alternatively, monoclonal antibody fragments can be synthesized using an automated peptide synthesizer. Exemplary fragments include, without limitation, a Fab fragment of antibody.

It also is contemplated that a molecular cloning approach may be used to generate monoclonal antibodies. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that more than $10^4$ times as many antibodies can be produced and screened in a single round, and that new specificities are generated by H and L chain combination which further increases the chance of finding appropriate antibodies.

The production of useful antibodies include those methods described, e.g., in U.S. Pat. No. 5,565,332, the disclosure of which is incorporated herein by reference in its entirety, and which describes the production of chimeric antibodies using a combinatorial approach; U.S. Pat. No. 4,816,567, the disclosure of which is incorporated herein by reference in its entirety, and which describes recombinant immunoglobulin preparations; and U.S. Pat. No. 4,867,973, the disclosure of which is incorporated herein by reference in its entirety, and which describes antibody-therapeutic agent conjugates.

Antibodies may be defined, in the first instance, by their binding specificity. Those of skill in the art can assess the binding affinity of a given antibody using techniques well known to those of skill in the art.

Antibody specificity relates to the *S. pneumoniae* serotype. There are 23 different serotypes represented by Pneumovax® 23, represented by the following designations: 1, 2, 3, 4, 5, 6B, 7F, 8, 9N, 9V, 10A, 11A, 12F, 14, 15B, 17F, 18C, 19F, 19A, 20, 22F, 23F, and 33F. The CDR region sequences for representative antibodies are set forth in U.S. Patent Application Publication No. 2013/0195876, the disclosure of which is incorporated herein by reference in its entirety.

In various embodiments, one may choose to engineer sequences of the identified antibodies or antibody binding fragments. The following is a general discussion of relevant techniques for antibody engineering.

Hybridomas may be cultured, then cells lysed, and total RNA extracted. Random hexamers may be used with reverse transcriptase (RT) to generate cDNA copies of RNA, and then PCR performed using a multiplex mixture of PCR primers expected to amplify all human variable gene sequences. PCR product can be cloned into pGEM-T Easy® vector, then sequenced by automated DNA sequencing using standard vector primers. Assay of binding and neutralization may be performed using antibodies collected from hybridoma supernatants and purified by fast protein liquid chromatography ("FPLC"), using Protein G columns.

Recombinant full length IgG antibodies can be generated by subcloning heavy and light chain Fv DNAs from the cloning vector into a second vector, such as a Lonza pConIgG1 or pConK2 plasmid vector, transfected into 293 Freestyle cells or Lonza CHO cells, and antibodies can then be collected and purified from the cell supernatants.

pCon Vectors™ are an easy way to re-express whole antibodies. The constant region vectors are a set of vectors offering a range of immunoglobulin constant region vectors cloned into the pEE vectors. These vectors offer easy construction of full length antibodies with human constant regions and the convenience of the GS System™.

Antibody molecules will comprise fragments (such as F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is an antibody derivative, e.g., an antibody comprising the CDR sequences identical to those in the disclosed antibodies (e.g., a chimeric or CDR-grafted antibody). In yet a further embodiment, the antibody is a fully human recombinant antibody. Alternatively, one may wish to make more subtle modifications, such as introducing conservative changes into an antibody molecule. In making such changes, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. It is understood that an amino acid can be substituted for another having a similar hydrophilicity and produce a biologically or immunologically modified protein. In such changes, the substitution of amino acids whose hydrophilicity values are within ±2, within ±1, or within ±0.5 may be employed.

Amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine, and isoleucine.

Modified antibodies may be made by any technique known to those of skill in the art, including expression through standard molecular biological techniques, or the chemical synthesis of polypeptides.

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alanine, serine, and glycine. However, other residues can function as well.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Antibodies developed for use in aspects described herein may be purified. The term "purified," as used herein, is intended to refer to a composition, isolatable from other components, where the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies, and the like or by heat denaturation, followed by centrifugation; gel filtration, reverse phase, hydroxylapatite and affinity chromatography; and combinations of such and other techniques.

In purifying an antibody, it may be desirable to express the polypeptide in a prokaryotic or eukaryotic expression system and extract the protein using denaturing conditions.

The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens my be used to simultaneously purify and select appropriate antibodies. Such methods often utilize the selection agent bound to a support, such as a column, filter, or bead. The antibodies are bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

Exemplary polysaccharide targets include, without limitation, capsular polysaccharides. For example, the capsular polysaccharide could include capsule type 6B or capsule type 19F.

As will be appreciated by those of skill in the art, the amount of antibody or antibody binding fragment bound to each discreet location on the chip can be optimized based on the surface area of the location where detection is to occur. By way of example, it is believed that optimal results can be achieved with a concentration of antibody and/or antibody binding fragment per location of about 50-800 pL.

Antibodies and/or antibody binding fragments that each bind specifically to one of two or more different serotypes of *Streptococcus pneumoniae* can be coupled to the array surface using any suitable chemistry for coupling antibodies and/or polypeptides. According to one embodiment, the antibodies or antibody binding fragments are covalently attached to the substrate.

Binding of the antibodies and/or antibody binding fragments to each discrete location can be carried out manually or using an automated system. For manual arraying, antibody solutions can be arrayed in a volume of ~1 µL at a final concentration of 1-500 µg/mL after a 1:1 dilution from a 2× stock (in modified phosphate-buffered saline ("MPBS")) into a solution containing 10% glycerol and 0.01% Tween®-20. After incubating for 10 minutes in an ambient environment, the chips can be immersed in a solution of blocking buffer (1 mg/mL bovine serum albumin ("BSA") in Hepes buffered saline ("HBS")) for 45 minutes and then rinsed with MPBS buffer containing an additional 3 mM EDTA and 0.005% Tween®-20 ("MPBS-ET"). For automated arraying, the antibody solutions can be arrayed by robotically printing using, e.g., piezoelectric spotting via a Scienion S3 arrayer or comparable method/device at a final concentration of, e.g., 50-800 pL, after a 1:1 dilution from a 2× stock (in MPBS) into a solution containing 0.01-1% (v/v) 12-crown-4 ether in MPBS. After incubating for 60 minutes at 70° F. and 70% relative humidity in the microarray chamber, the chips can be immersed in a solution of blocking buffer (BSA in HBS) for 60 minutes and then rinsed with MPBS-ET.

According to other aspects illustrated herein, there is provided a sensor chip suitable for serological detection of *Streptococcus pneumoniae*. The sensor chip includes a substrate comprising a surface comprising bound thereon antibodies or antibody binding fragments that each bind specifically to one of two or more different serotypes of *Streptococcus pneumoniae*. In certain embodiments, the antibodies or antibody binding fragments bind specifically to *Streptococcus pneumoniae* polysaccharides. The antibodies or antibody binding fragments are attached to the surface at different locations. The surface forms a coating that results in destructive interference of polarized light illuminating the surface at an appropriate incident angle and wavelength in the absence of *Streptococcus pneumoniae* binding. Exposure of the surface to a sample comprising *Streptococcus pneumoniae* to which the antibodies or antibody binding fragments bind produces a detectable change in reflectance at a location upon antibody or antibody binding fragment binding.

The arrays disclosed herein are particularly useful as a diagnostic tool for pneumonia and pneumococcal capsule typing.

Once the array is prepared, the sensor chip can be exposed to serum samples obtained from individuals (or diluted serum samples), and then the presence (or absence) of one or more serotypes of *Streptococcus pneumoniae* can be determined based on the detection of a change (or lack of change) in the detector output following exposure of the sensor chip to the serum sample. As is well known in the art, the absence of a detectable signal does not necessarily mean that *Streptococcus pneumoniae* is not present but rather that it is below detectable limits and, therefore, is not likely to be present. The image capture can be achieved by any of the detection systems described above, e.g., via an image array detector that captures an image of at least a substantial portion of the surface of the chip. For arrays of hundreds to hundreds of thousands of probes, an automated chip reader can be programmed to assess the change in reflectivity for each spot on an array based on the captured image.

Detection may be carried out using an AIR detection system, an SPR detection system, a BASI detection system, or ellipsometry detection system.

Thus, according to aspects illustrated herein, there is provided a method for detecting serotypes of *Streptococcus pneumoniae* using arrayed imaging reflectometry (AIR). This method involves providing a sensor chip as described herein. The sensor chip is contacted with a sample under conditions that permit specific binding to *Streptococcus pneumoniae* surface antigen by the antibodies or antibody binding fragments present on the chip surface. Light reflected off the surface of the chip is detected under conditions effective to identify specifically bound *Streptococcus pneumoniae* surface antigen, thereby detecting a serotype of *Streptococcus pneumoniae*.

As used herein, the individual from which serum samples are obtained can be any animal that is susceptible to infection by *Streptococcus pneumoniae*, including humans and non-human primates, livestock, domesticated animals, and wild animals. The serum sample can be obtained from both living individuals and a corpse post-mortem.

In one embodiment, methods described herein further involve rinsing the sensor chip to remove any *Streptococcus pneumoniae* surface antigen not specifically bound by the antibodies or antibody binding fragments.

Detecting pursuant to the methods described herein may involve, according to one embodiment, measuring light reflected from the chip and providing an output identifying specifically bound *Streptococcus pneumoniae* surface antigen based on the measured reflected light, including its location and the intensity of the reflected light. In one embodiment, measuring the reflected light further comprises capturing an image of at least a substantial portion of the surface of the chip.

Further analysis can include, without limitation, ELISA, PCR, realtime-PCR, mass spectrometry, and liquid chromatography-NMR spectroscopy.

EXAMPLES

Aspects illustrated herein may be further illustrated by reference to the following examples.

Example 1—Pneumococcus Serology Array

Figure 4A:
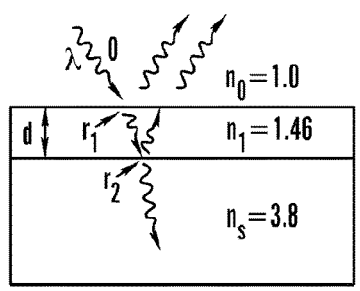
FIGS. 4A-C are schematic illustrations of one embodiment of AIR. In particular.
Figure 4B:
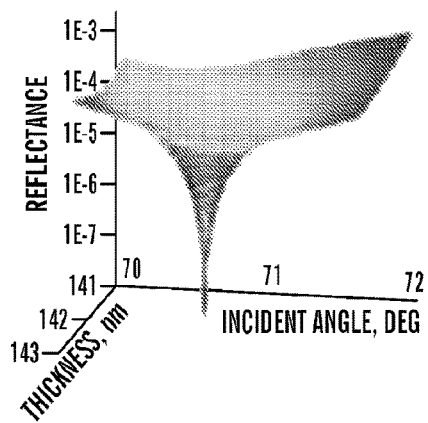
Figure 4C:
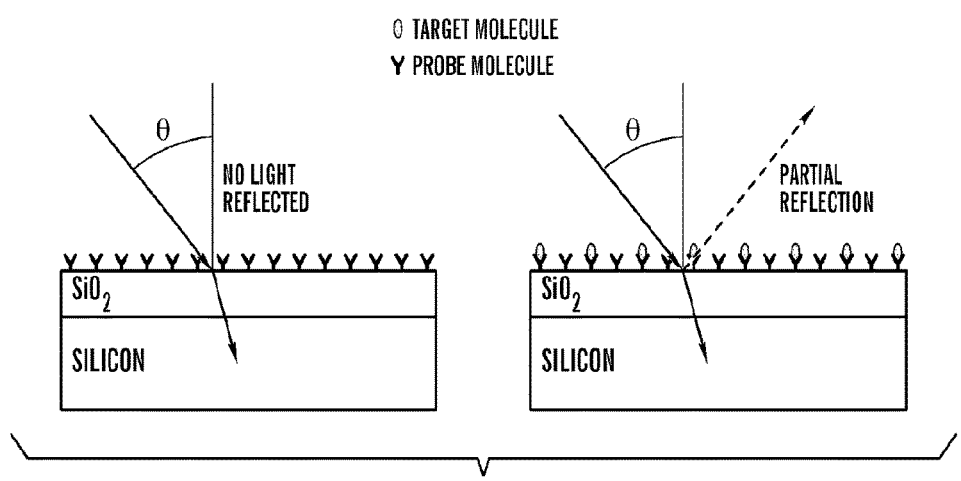

The pneumococcal diagnostic array is built on the Arrayed Imaging Reflectometry (AIR) platform, which is a simple, sensitive, multiplex technique for label-free analysis of molecular interactions. The AIR sensor is based on the binding-induced perturbation of an antireflective coating on the surface of a silicon chip. In brief, a near null reflectivity condition may be obtained by carefully matching the incident angle and wavelength of s-polarized light to the optical thickness of a dielectric material on the silicon surface (FIGS. 4A-C). This is obtained by using a helium neon laser ($\lambda$=632.8 nm) at a 70.6 degree incident angle, and a dielectric layer ($SiO_2$ plus antibodies) thickness of 1419 Å. Highly reproducible methods have been developed for preparing $SiO_2$ layers that are extremely flat, with Ångstrom level control of thickness. Likewise, robust vapor and solution phase chemical deposition strategies allow one to immobilize many classes of functional capture molecules.

As AIR is an imaging technique, an array of as many as 1000 spots can be "read" in a matter of milliseconds. This provides a particular advantage over techniques such as spectroscopic ellipsometry, angle-scanning SPR, or OI-RD (oblique incidence-reflectivity difference); the scanning requirements of those methods require significantly longer acquisition times. The significant advantages of AIR over other label-free systems under development include (1) multiplex capability: target multiplexing is simply a matter of increasing the number of spots on the chip, while sample multiplexing could in principle be implemented in a 96-well system; (2) instrument simplicity: the optical system has no moving parts, no need for temperature control, and can be constructed from off-the-shelf components costing<$3000; and (3) simple chip manufacture: AIR employs base materials from the microelectronics industry, and no photo- or E-beam lithography is required, unlike ring resonators, cantilevers, and most 2-D photonic crystals.

The array includes a grid of serotype-specific anti-pneumococcus polysaccharide spots formed on a pre-functionalized AIR chip. The array also incorporates a number of spots serving as positive and negative controls; anti-human IgG and anti-fluorescein are representative examples of the former and the latter. Exposure of the array to a human serum thought to contain pneumococcus followed by rinsing, drying, and imaging in an AIR reflectometer reveals the presence of specific serotypes based on increased reflective intensity in specific array spots.

Figure 5:
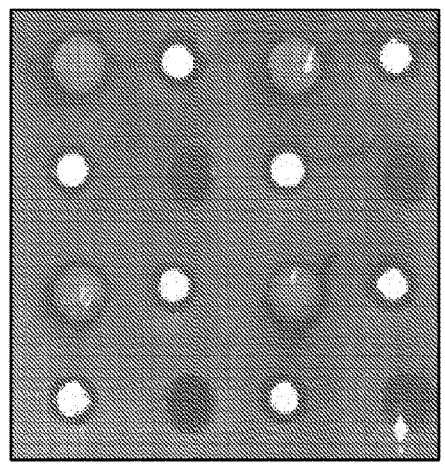
FIG. 5 is a photograph showing a preliminary demonstration of an AIR array for the detection of pneumococcus. Bright spots are anti pneumococcus antibodies responding to the presence of PS6A polysaccharide doped in human serum.

To provide an initial assessment of the ability of AIR arrays to detect pneumococcal antigens, two antibodies (one IgG and one IgM) were immobilized against two pneumococcal polysaccharides derived from serotypes 14 and 6A, respectively. Anti-human IgG was included on the array as a positive control, while anti-fluorescein isothiocyanate (anti-FITC) was printed as a negative control. Exposure of the array to pooled normal human serum (PNHS) diluted 1:4 with assay buffer (PBS plus Tween®-20) doped with antigen followed by imaging of the array showed selective detection of the appropriate polysaccharide (FIG. 5). Initial experiments suggest that pg/mL detection is possible.

Example 2—Successful Production and Use of Antibody AIR Arrays

Figure 6:
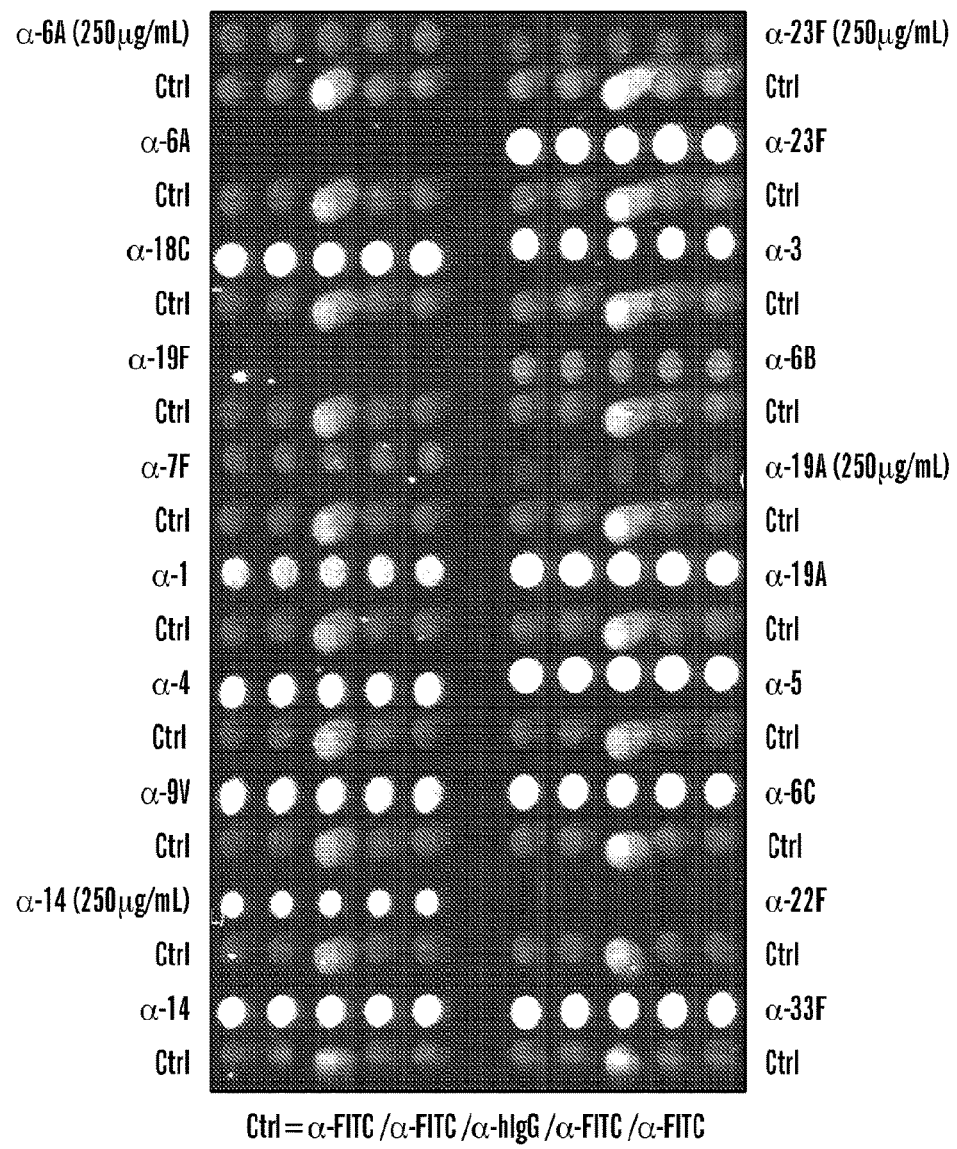
FIG. 6 is a photograph demonstrating a 20-plex pneumococcus antibody array on the AIR platform. Note that some antibodies in this image have been printed too thick (as evidenced by saturated brightness). Further efforts have improved the deposition behavior of those antibodies. Here "Ctrl" rows feature four anti-fluorescein spots (negative control) surrounding one anti-IgG spot (positive control).

Building on preliminary data, it was next sought to produce a more complex array. Antibodies to 20 Pneumococcus serotypes were arrayed using a Scienion S3 piezoelectric printer at stock concentrations ranging from 250 micrograms/mL to 500 micrograms/mL on amine-reactive Adarza BioSystems AIR chips. A representative image of an AIR array produced in this manner is shown in FIG. 6.

Materials and Methods

Substrates were prepared from a 5×6 mm silicon chip with thermally grown $SiO_2$ that was etched to ~1360 Å with hydrofluoric acid (HF). The surface was functionalized with ~7.5 Å of succinic anhydride (SA) via chemical vapor deposition (CVD). The post-functionalized thickness of the substrate was ~1373 Å.

For the probes, immunoglobulin from mouse hybridoma cell lines specific for the capsular polysaccharides of various serotypes of *Streptococcus pneumoniae* were used. The probes are kept at 4° C. at stock concentration (1100-2000 μg/mL). The probes were prepared at ~500 μg/mL in 1×m PBS with a pH of 5.5.

There were two control probes used in the assay, which were prepared the same way as the target probes. The negative control was anti-fluorescein isothiocyanate (anti-FITC), and the positive control was anti-human IgG.

The target was lysate from *Streptococcus pneumoniae* grown in Todd Hewitt Media (THM), stored at ~20° C., and prepared as follows. Lysates were thawed at room temperature, homogenized via inversion/vortexing, and a 1 mL aliquot was made (also stored at −20° C.). When needed, the aliquot was thawed, centrifuged for 5 minutes at 10 k RPM, and supernatant was drawn off to prepare the target solution: 1% or 5% blood loss (BL) in autologous whole blood (AWB) with 5% pooled normal human serum (PNHS) to build thickness and activate the positive control probes. The control target contained only pooled normal human serum (PNHS) in autologous whole blood (AWB).

For the arrayer, a Scienion S3 microarrayer that works through piezoelectric dispensing was used. The system was backed with 0.22 μm-filtered nanopure water (17.5 mOhm) that was degassed through autoclaving. The system was kept at 65% relative humidity during printing.

For each spot, a drop of probe solution was dispensed by the arrayer onto the substrate at a volume of ~450 pL. There were typically 5 spots per probe on each chip, flanked by 4-8 negative controls.

The assay was carried out in a 96-well plate. Washes, blocking, and exposure to target were done on the plate, with one chip per well. The plate was kept at room temperature on an orbital shaker with a speed of 65 RPM.

Procedure

Substrates were placed in the arrayer and spotted with probe solution. The substrates were then adhered to a strip with adhesive backing Once all the substrates were adhered, they were submerged into wells containing NaOAc buffer at a pH 5 (no shaking). After ~1 minute, the substrates were moved to wells containing 1% BSA in NaOAc buffer (pH 5) and allowed to block for 30 minutes while shaking.

Substrates were moved to wells containing 1× autologous whole blood (AWB) and washed for 5 minutes while shaking Substrates were then moved to wells containing target solution and allowed to incubate for 60 minutes while shaking Substrates were then moved to wells containing 1× autologous whole blood (AWB) and washed for 10 minutes while shaking (Wash Test 2 saw a reduction in cross-reactivity when substrates were washed for 15 minutes at a higher rotational speed (~230 RPM).)

Substrates were removed from the plate and washed with 0.22 μm-filtered nanopure water. Tweezers were used to grasp the substrate-adhered strip and move it through the water 5 times clockwise, 5 times back and forth, and another 3 times clockwise. Substrates were then dried with a stream of $N^2$ gas, removed from the adhesive strip, and placed in a chip holder.

Substrates were imaged with a prototype open-sky reader at several exposures, with 500 ms being the most usable under the conditions described.

Median intensity of spots from image were converted to thickness using model data generated by Adarza Biosystems. The difference between experimental and local control spots on a target-exposed chip was compared to the difference between experimental and control spots on a control-expressed chip to determine if any detection had occurred.

FIG. 6 shows an initial demonstration of the successful immobilization of antibodies to 16 serotypes on an AIR chip. The serotype targeted by each antibody is listed at the margin; each antibody was immobilized in 5 replicate spots. As an example of methods that can be used to reduce the thickness of antibody spots, although most antibodies were immobilized at concentrations of 500 micrograms/mL, some were also immobilized at concentrations of 250 micrograms/mL. This allows one to reduce the thickness of antibodies immobilizing with very high efficiency and, therefore, producing a saturated response in the AIR signal (for example, 500 micrograms/mL anti-23F) to produce a spot thickness closer to the reflective minimum (anti-23F, 250 microgram/mL).

Example 3—Demonstrated Detection of Purified Capsular Polysaccharide

Results of an array to detect the capsular polysaccharide corresponding to serotype 33F, extracts of arrays imaged without exposure (control, top) and following exposure (Experimental, bottom) to purified 33F capsular polysaccharide in Todd-Hewitt media/MPBS are shown in FIG. 7. Mean intensity for one selected spot increased from 22697 to 35644. Very little change in the intensity of the negative control spots was observed. This indicates specific detection of the 33F capsular polysaccharide.

Example 4—Cross-Reactivity Assessment

Figure 8A:
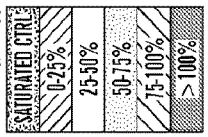
Figure 8B:
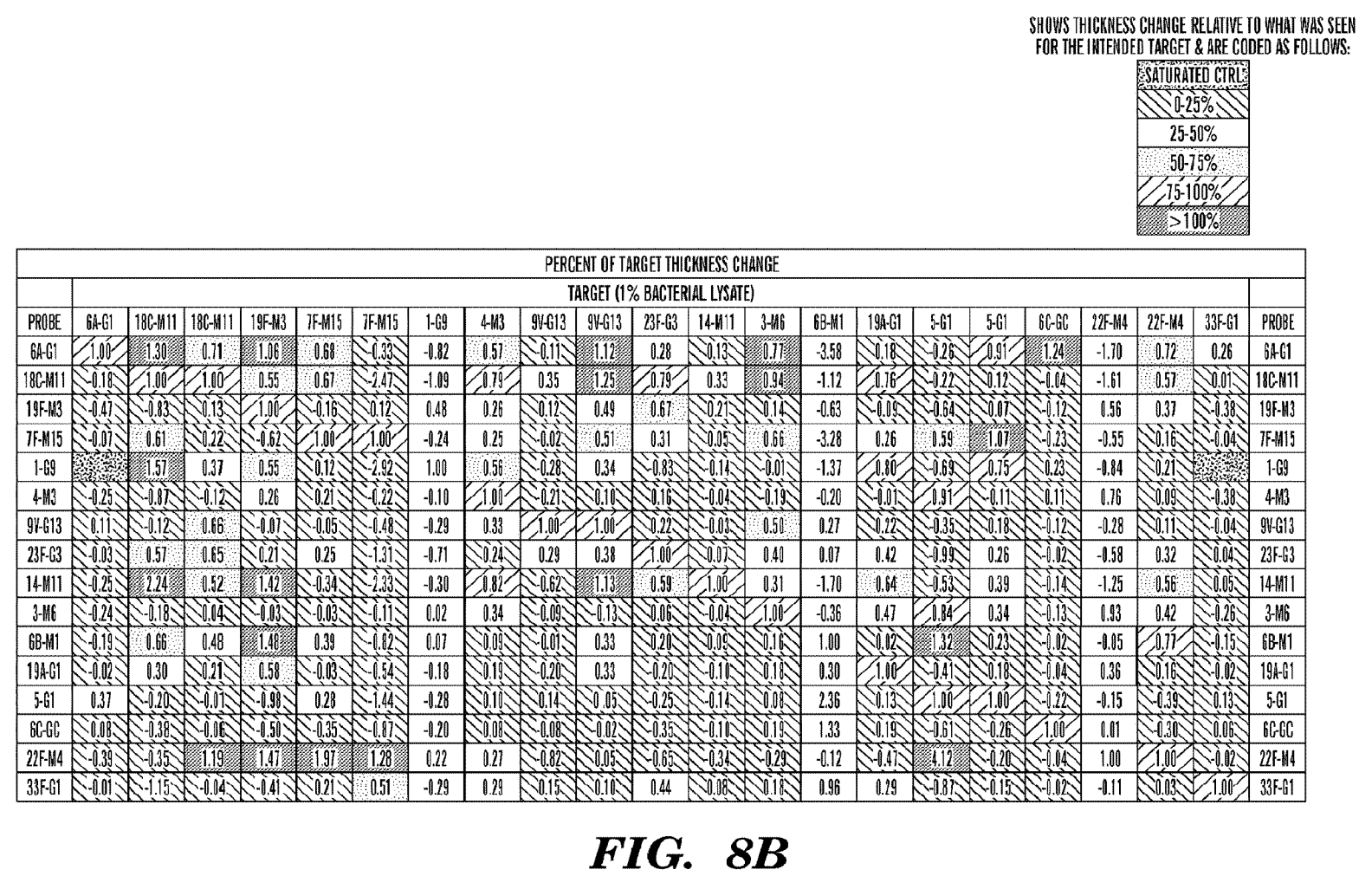

To assess array performance and antibody cross-reactivity, arrays were exposed to 1% or 5% solutions of bacterial lysate in MPBS buffer containing 10% pooled normal human serum as a carrier. Preliminary results expressed as a function of percentage of desired target thickness (intensity) are shown in FIGS. 8A-B for each serotype tested. Some of the observed cross-reactivity will be diminished through further optimization of experimental protocols, including both aspects of the incubation and washing steps.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed:

1. An arrayed imaging reflectometry (AIR) sensor chip suitable for serological detection of *Streptococcus pneumoniae* comprising:
    a multilayer substrate comprising a surface; and
    antibodies or antibody binding fragments covalently bound to said surface at different locations, wherein each antibody or antibody binding fragment binds specifically to one of two or more different serotypes of *Streptococcus pneumoniae*, wherein the surface forms a coating that results in destructive interference of polarized light illuminating the surface at an appropriate incident angle and wavelength in the absence of *Streptococcus pneumoniae* binding, and wherein exposure of the surface to a sample comprising *Streptococcus pneumoniae* to which the antibodies or antibody binding fragments bind produces a detectable change in reflectance at a location upon antibody or antibody binding fragment binding.

2. The sensor chip according to claim 1, wherein the antibodies or antibody binding fragments bind specifically to pneumococcal polysaccharides.

3. The sensor chip according to claim 2, wherein the pneumococcal polysaccharides are full length polysaccharides.

4. The sensor chip according to claim 2, wherein the pneumococcal polysaccharides are polysaccharide fragments.

5. The sensor chip according to claim 2, wherein the pneumococcal polysaccharides are capsular polysaccharides.

6. A method for detecting serotypes of *Streptococcus pneumoniae* using arrayed imaging reflectometry (AIR), said method comprising:
    providing a sensor chip according to claim 1;
    contacting the sensor chip with a sample under conditions that permit specific binding to *Streptococcus pneumoniae* surface antigen by the antibodies or antibody binding fragments present on the chip surface; and
    detecting light reflected off the surface of the chip under conditions effective to identify specifically bound *Streptococcus pneumoniae* surface antigen, thereby detecting a serotype of *Streptococcus pneumoniae*.

7. The method according to claim 6 further comprising:
    rinsing the sensor chip to remove any *Streptococcus pneumoniae* surface antigen not specifically bound by the antibodies or antibody binding fragments.

8. The method according to claim 6, wherein the sample is obtained from a human, a non-human primate, a domesticated animal, or a wild animal.

9. The method according to claim 6, wherein said detecting comprises:
    measuring light reflected from the chip and
    providing an output identifying specifically bound *Streptococcus pneumoniae* surface antigen based on the measured reflected light.

10. The method according to claim 9, wherein the measuring the reflected light further comprises capturing an image of at least a substantial portion of the surface of the chip.

11. The sensor chip according to claim 1, wherein the antibodies or antibody binding fragments are bound directly to the surface.

12. The sensor chip according to claim 1, wherein the antibodies or antibody binding fragments are positioned to bind to the one of two or more different serotypes of *Streptococcus pneumoniae*.

* * * * *

UNITED STATES PATENT AND TRADEMARK OFFICE
CERTIFICATE OF CORRECTION

PATENT NO.          : 10,209,254 B2
APPLICATION NO.     : 15/028370
DATED               : February 19, 2019
INVENTOR(S)         : Benjamin L. Miller and Moon H. Nahm Page 1 of 1

It is certified that error appears in the above-identified patent and that said Letters Patent is hereby corrected as shown below:

In the Specification

At Column 1, Line 11, please insert the following:
--This invention was made with government support under AI030021 awarded by the National Institutes of Health. The government has certain rights in the invention.--

Signed and Sealed this
Sixteenth Day of April, 2019

Andrei Iancu
*Director of the United States Patent and Trademark Office*